United States Patent
Carlsson et al.

(10) Patent No.: US 9,539,175 B2
(45) Date of Patent: Jan. 10, 2017

(54) CONTAINER AND CONNECTOR FOR PROVIDING A MEDICAL SOLUTION

(75) Inventors: Per-Olov Carlsson, Ronneby (SE); Thore Falkvall, Helsingborg (SE); Björn Gillerfalk, Ronneby (SE)

(73) Assignee: METPRO AB, Lund (SE)

( * ) Notice: Subject to any disclaimer, the term of this patent is extended or adjusted under 35 U.S.C. 154(b) by 119 days.

(21) Appl. No.: 14/127,826

(22) PCT Filed: Jun. 25, 2012

(86) PCT No.: PCT/EP2012/062275
§ 371 (c)(1),
(2), (4) Date: Mar. 12, 2014

(87) PCT Pub. No.: WO2012/175753
PCT Pub. Date: Dec. 27, 2012

(65) Prior Publication Data
US 2014/0175126 A1    Jun. 26, 2014

(30) Foreign Application Priority Data
Jun. 23, 2011  (EP) ..................................... 11171247

(51) Int. Cl.
*B67D 7/78*    (2010.01)
*A61J 1/20*    (2006.01)
(Continued)

(52) U.S. Cl.
CPC ................ *A61J 1/2089* (2013.01); *A61J 1/10* (2013.01); *A61J 1/1475* (2013.01); *A61J 1/2093* (2013.01);
(Continued)

(58) Field of Classification Search
CPC .......... A61J 1/2089; A61J 1/1475; A61J 1/10; A61J 1/2093; A61J 1/202; A61J 1/2027; A61J 1/2024; A61M 1/167; A61M 1/1666; A61M 39/10; A61M 39/105; A61M 39/1011; A61M 2206/20
(Continued)

(56) References Cited

U.S. PATENT DOCUMENTS

| 5,121,857 A | * | 6/1992 | Hutchinson | .......... | B67D 1/0055 |
| | | | | | 222/105 |
| 5,794,669 A | * | 8/1998 | Polaschegg | .......... | A61M 1/1656 |
| | | | | | 141/100 |

(Continued)

FOREIGN PATENT DOCUMENTS

| DE | 10 2009 058445 A1 | 6/2011 |
| EP | 1 344 550 A1 | 9/2003 |
| WO | WO 00/57833 A1 | 10/2000 |
| WO | WO 2007/144427 A2 | 12/2007 |

*Primary Examiner* — Kevin P Shaver
*Assistant Examiner* — Robert Nichols, II
(74) *Attorney, Agent, or Firm* — Knobbe, Martens, Olson & Bear, LLP (57) ABSTRACT

A container for mixing an enclosed medical agent with a fluid. The container comprising an inclining bottom seam directed towards a connector. The connector comprising an elongated hollow body having a plurality of interconnected walls defining a first and a second longitudinal flow channel for fluidly connecting an inside and an outside of the container. The first flow channel has a first opening and a second opening, the first opening of the first flow channel is devised to be arranged inside of the container and the second opening of the first flow channel is devised to be arranged outside the container. The first opening of the first flow channel is arranged radially outwards from the first flow channel and directed towards said inclined bottom seam. The second flow channel has a first opening devised to be arranged inside of said container and a second opening devised to be arranged outside the container arranged axially to the first opening of the second flow channel.

29 Claims, 9 Drawing Sheets

(51) Int. Cl.
  *A61M 1/16*   (2006.01)
  *A61M 39/10*  (2006.01)
  *A61J 1/10*   (2006.01)
  *A61J 1/14*   (2006.01)

(52) U.S. Cl.
  CPC ........... *A61M 1/167* (2014.02); *A61M 1/1656* (2013.01); *A61M 1/1666* (2014.02); *A61M 39/10* (2013.01); *A61J 1/202* (2015.05); *A61J 1/2024* (2015.05); *A61J 1/2027* (2015.05); *A61M 39/105* (2013.01); *A61M 39/1011* (2013.01); *A61M 2206/20* (2013.01)

(58) Field of Classification Search
  USPC ............................. 222/129, 185.1, 94, 145.5
  See application file for complete search history.

(56) References Cited

U.S. PATENT DOCUMENTS

| | | | | |
|---|---|---|---|---|
| 6,007,529 | A * | 12/1999 | Gustafsson | A61J 1/00 |
| | | | | 206/219 |
| 6,591,874 | B2 * | 7/2003 | Credle, Jr. | B65D 75/5883 |
| | | | | 141/10 |
| 2005/0224372 | A1 | 10/2005 | Sasso et al. | |
| 2006/0052738 | A1 | 3/2006 | Ramella | |
| 2007/0278114 | A1 * | 12/2007 | Kane | B65D 25/08 |
| | | | | 206/219 |
| 2007/0299419 | A1 * | 12/2007 | Vancaillie | A61J 1/2089 |
| | | | | 604/416 |
| 2009/0057347 | A1 * | 3/2009 | Leys | B65D 83/0055 |
| | | | | 222/386.5 |

\* cited by examiner

CONTAINER AND CONNECTOR FOR PROVIDING A MEDICAL SOLUTION

RELATED APPLICATIONS

This application is the U.S. National Phase under 35 U.S.C. §371 of International Patent Application No. PCT/EP2012/062275, filed on Jun. 25, 2012, and published in English on Dec. 27, 2012 as WO 2012/175753, which claims priority to European Application No. 11171247.7, filed Jun. 23, 2011. The contents of these applications are expressly incorporated herein by reference in their entireties.

BACKGROUND OF THE INVENTION

Field of the Invention

This invention pertains in general to the field of providing solutions, particularly medical solutions. More particularly the invention relates to a multi compartment container and a connector, as well as a method, for providing a medical solution, such as a dialysate solution.

Description of the Related Art

EP2035059 discloses a container comprising a plurality of compartments separated by compartment dividers, and an inlet connector for receiving a liquid via a connection tube. The compartment dividers rupture when a sufficient pressure is applied by a liquid or gas introduced into the container through the inlet connector. Some of the compartments comprise powder, which dissolves at the introduction of liquid into the container.

The disclosed container has vertically positioned compartment dividers which is not always an optimal arrangement for providing a thoroughly mixing of a solution. Further, the connection to the mixing system is made by either separated inlets or outlets or by alternating a flow through an inlet being a tube by a valve or a pump. The document also discloses a double lumen connector being two cannulas. But there is no teaching of how to configure the combined inlet/outlet and how to arrange the inlet/outlet in relation to the features of the container to obtain an optimized mixing and/or improve control of the opening of the peelable dividers.

Thus, there is a need for an improved solution to the container and connector combination to obtain a better mixing of a solution inside the container. It is also desired to improve the precision and quality of the final medical solution for providing to a patient. The improvement should also provide for time savings by decreasing the dissolving time and thus the effectiveness of the mixing. The invention may also be seen as an alternative to what is hitherto available, preferably more cost-effective.

Hence, an improved combination of a container and connector would be advantageous and in particular for improving the quality of a medical solution and allowing for increased flexibility and effectiveness would be advantageous.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing devices and methods according to the appended patent claims.

According to a first aspect, a container is provided for mixing an enclosed medical agent with a fluid. The container has an inclining bottom seam directed towards a connector. The connector includes an elongated hollow body having a plurality of interconnected walls defining a first and a second longitudinal flow channel for fluidly connecting an inside and an outside of the container. The first flow channel has a first opening and a second opening, the first opening of the first flow channel is devised to be arranged inside of the container and the second opening of the first flow channel is devised to be arranged outside the container. The first opening of first flow channel is arranged radially outwards from the first flow channel and directed towards the inclined bottom seam. The second flow channel has a first opening devised to be arranged inside of the container and a second opening devised to be arranged outside the container arranged axially to the first opening of the second flow channel.

According to an aspect of the disclosure, a fluid connector device is provided for a container. The connector comprises an elongated hollow body having a plurality of interconnected walls defining a first and a second longitudinal flow channel fluidly connecting an inside and an outside of the container. The first flow channel has a first opening and a second opening, the first opening of the first flow channel is devised to be arranged inside of the container and the second opening of the first flow channel is devised to be arranged outside the container. The first opening of first flow channel is arranged radially outwards from the first flow channel. The second flow channel has a first opening devised to be arranged inside of the container and a second opening devised to be arranged outside the container arranged axially to the first opening of the second flow channel. The body comprises a tapered protruding member, a fastening section for fastening the connector device to the container, and a directing section positioned adjacent to the first opening of the first flow channel for directing a flow of a fluid through the first opening of the first flow channel.

In some embodiments, the first opening of the first flow channel is circumferentially positioned around an outer surface of a wall of the first flow channel.

In some embodiments, the first flow channel has an axially decreasing flow cross-section towards the first opening, and/or wherein a first wall surrounding the second flow channel is conically tapering towards the outside of the container and the first wall is an interior wall of the first flow channel and a second wall is surrounding the first flow channel without tapering to provide the axially decreasing flow cross-section.

In some embodiments the fastening section is adapted to be attachable to a bottom seam of the container.

In some embodiments, the directing section is further including a distancing unit for keeping a wall of the container at a distance from the first opening of the first flow channel. In this manner, unintended fluid stop is prevented.

In some embodiments, the connector is operable in different operation modes, including a first operation mode, wherein the first channel and the second channel inlet channels; a second operation mode, wherein the first channel is an inlet and the second channel is an outlet; and/or a third operation mode, wherein the first channel and the second channel are outlets.

In some embodiments, the second elongate body is arranged longitudinally inside the first elongate body and having a first end and a second end.

In some embodiments, first ends of the first and second elongate bodies are axially offset, and/or wherein the second elongate body is arranged coaxially inside the first elongate body, and/or wherein the second fluid channel is a central through channel.

In some embodiments, the fluid connector device is a combined inlet and outlet connector, and/or the first and second bodies are integrally in a single monolithic unit. This provides for advantageously cheap manufacture of the device.

In some embodiments, the first opening of the second flow channel is axially offset towards the interior from the first opening of the first flow channel. In this manner, the length of the protruding end into the container can be adjusted for optimal mixing.

In some embodiments, an internal axial recess is arranged at the first flow channel's first opening. This provides for an improved mixing thanks to a more turbulent flow.

In some embodiments, the directing means is arranged for providing a substantially lateral flow entering the container when the first flow channel is an inlet. The second flow channel may be an inlet or an outlet at the same time in different operation modes. This provides for an advantageous flow pattern for mixing.

According to another aspect of the disclosure, a container for providing a medical solution to be mixed in the container is provided. The container comprises preferably a fluid connector device according to the first aspect of the invention. The container has at least two substantially longitudinally positioned and peelable compartment dividers arranged to releasably separate at least three longitudinal compartments of the container. A plurality of compartments is subdivided by the compartment dividers, wherein at least a first compartment of the three longitudinal compartments contains a powder substance to be mixed with a liquid to provide the medical solution. At least a fourth compartment adjacent the three longitudinal compartments are empty from a substance prior to mixing the medical solution. The fluid connector device is arranged at a bottom of the container for connection of the container to a liquid providing system. The fluid connector is in fluid communication with the second compartment only prior to a mixing operation for providing the medical solution, and wherein the connector is arranged to come into fluid communication with the three longitudinal compartments upon supplying a liquid pressure through the fluid connector for simultaneously opening the compartment dividers. In this manner, a quick and reliable high quality mixing is provided. No separate mixing container is needed. Dissolving of powder substances I provided very effectively without risk for residual particles.

In some embodiments, the container is a flexible bag. The container may has beveled and/or rounded lower edges. The fluid connector is advantageously arranged at a bottom seam of the container (in operation of the container). The flexible bag's walls may be made of a laminate having an outer layer of Polyethylene terephthalate (PET) polymer and an inner layer of polyethene. There is no polyamide reinforcement layer.

In some embodiments, the empty compartment is obtained by a substantially vertically positioned compartment divider and parts of two longitudinally compartment dividers.

In some embodiments, the empty compartment is obtained singly by a curved, i.e. not straight, compartment divider or by the curved compartment divider in combination with parts of two longitudinally compartment dividers.

In some embodiments, the compartment dividers of the empty compartment are arranged to open completely when enough pressure of a fluid is applied.

In some embodiments, the compartment dividers are adapted to open either simultaneously and/or subsequently in a defined sequence.

In some embodiments, the compartment dividers are fully open when a mixing action starts.

In some embodiments, the container is made of two layers of material and wherein the compartment dividers are welded by applying a level of heat and the strength of the compartment dividers are controlled by the level of applied heat. The flexible bag's walls may in particular for this purpose be made of a laminate having an outer layer of Polyethylene terephthalate (PET) polymer and an inner layer of polyethene.

In some embodiments, at least two compartments of the at least four comprises a powder and at least one of the three compartments comprises a solution.

According to a further aspect of the disclosure, a combination of a connector of the first aspect of the invention, and a container of the second aspect of the invention is provided. The connector is fastened to the bottom seam of the container by the fastening section of the tapered protruding member, and wherein the fluid direction section are arranged to direct a flow of a fluid towards the beveled and/or rounded lower edges and thereby create a circulatory circulation in the container.

According to another aspect of the disclosure, a method is provided for obtaining a medical solution using a combination of the third aspect of the invention. The method comprises several operation modes for this purpose. In a first operation mode a flow of a fluid is introduced into the container through a first and second channel of the connector communicating with a fluid source. Compartment dividers are opened of an empty compartment and subsequently the longitudinal compartment dividers by a pressure created by a volume of fluid introduced into the container through the connector caused by the flow. A turbulent circulatory circulation is obtained in the container by directing the flow of the fluid towards the beveled and/or rounded lower edges using the direction section. The introduction of the fluid is stopped when a predetermined volume is introduced into the container. A second operation mode comprises mixing a content of the container including the introduced fluid by re-circulation of the content for obtaining the medical solution, including simultaneously using the connector as an combined inlet and outlet for the re-circulation by the first channel operating as an inlet and the second channel as an outlet, whereby a second turbulent circulatory circulation is obtained in the container for the mixing.

In yet a further aspect of the disclosure, a method is provided for obtaining a medical solution. The method comprises preferably using a container according to any of the above aspects. The method comprises a first operation mode comprising introducing a flow of a fluid into the container through a first and/or second channel of the connector communicating with a fluid source; opening compartment dividers of an empty compartment and subsequently compartment dividers by a pressure created by a volume of fluid introduced into the container through the connector, obtaining a turbulent circulatory circulation in the container by directing the flow of the fluid towards an inclined bottom seam and/or beveled edges of the container, stopping the introduction of the fluid when a predetermined volume is introduced into the container. In a second operation mode the method comprises mixing a content of the container including the introduced fluid by re-circulation of the content for obtaining the medical solution, including simultaneously using the connector as an combined inlet and outlet for the re-circulation by the first channel operating as an inlet radially directing the fluid towards the inclined bottom seam and/or beveled edges, and the second channel as an outlet, whereby a second turbulent circulatory circulation is obtained in the container for the mixing.

In some embodiments, the second turbulent circulatory circulation is a flow circulation pattern comprising a turbulent flow flowing radially outward from the first channel of the connector, up along an outer edge towards a top section of the container, turning inwardly towards a central section of the container and flowing back down to the connector for leaving the container towards a re-circulation pump via the second channel of the connector, and from the re-circulation pump back to the first channel of the connector for continued internal circulation in the container.

Thus an effective mixing is achieved.

The mixing system comprising the pump may be of the type disclosed in EP2035059, which is incorporated herein by reference in its entirety.

According to a fifth aspect of the invention, a method is provided. The method is a method for emptying a provided medical solution obtained according to the fourth aspect of the invention, a combination according to the third aspect of the invention. The method comprises stopping the re-circulating action; and emptying the medical solution from the container through the connector in a third operation mode, wherein the first channel and the second channel of the connector are outlets.

A large flow for emptying the container is thus possible. The container may be completely emptied leaving minimum residues in the container for recycling or disposal. This is environmentally advantageous.

Further embodiments of the invention are defined in the dependent claims, wherein features for the second and subsequent aspects of the invention are as for the first aspect mutatis mutandis.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DETAILED DESCRIPTION OF PREFERRED EMBODIMENTS

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art.

The following description focuses on embodiments of the present invention applicable to be used with a dialysis system and in particular to the preparation of a dialysis liquid or dialysate concentrates of different concentrations using powder concentrates. However, it will be appreciated that the invention is not limited to this application but may be applied to many other examples of systems were it may be an advantage to provide powders to be mixed with a liquid to be used with, for example, a solution providing system. Thus, medical solutions prepared by the exemplary embodiments described below may be used in dialysis treatments, as concentrate solutions or ready-made solutions for dialysis, as infusion solutions, such as Ringer's lactate, as nutrition solutions, as replacement solutions, as plasma expander solutions, etc.

FIG. 1A-G is showing an exemplary embodiment of a connector 10. The connector 10 is made of an elongated body 22 having interconnected walls to provide two flow channels, preferably being two elongated hollow bodies.

One of the hollow bodies is positioned axially arranged inside the other hollow body.

In the illustrated example, the cross section of both bodies is circular forming annular bodies. The bodies are in the illustrated example arranged co-axially. The bodies may in other examples have any shape of its cross-section, such as ellipsoid, or annular, or polygonal etc.

A proximal end (shown in the upper portion of FIG. 1A) of the connector 10 is arranged to be positioned inside a container and a distal end (shown in the lower portion of FIG. 1A) to be positioned outside of the container. At the distal end, the connector is provided with two openings 16, 17. Preferably the openings 16, 17 are annular-shaped, but may additionally and/or alternatively be ellipsoid or polygonal. Additionally one of the bodies may be substantially centrally positioned, here the opening 16 of a first body, in relation to the opening 17 of the other body. In the illustrated example, the end edge of the first opening 16 of the inner body is axially recessed in relation to the end edge of the other opening 17 of the outer body. This may provide for a mechanical protection of the inner body, as well as a keying of the connection in order to provide a safety feature for preventing connection to non-compatible mixing systems. Additionally, there are two openings 11, 13 at the proximal end of the connector 10. One of the openings 11 is positioned along a longitudinal axis of the connector 10 and the other opening 13 may be positioned radially outwards from the outer elongated body 22. Preferably, the radially positioned opening 13 may surround the outer elongated body 22 circumferentially.

Figure 1A:
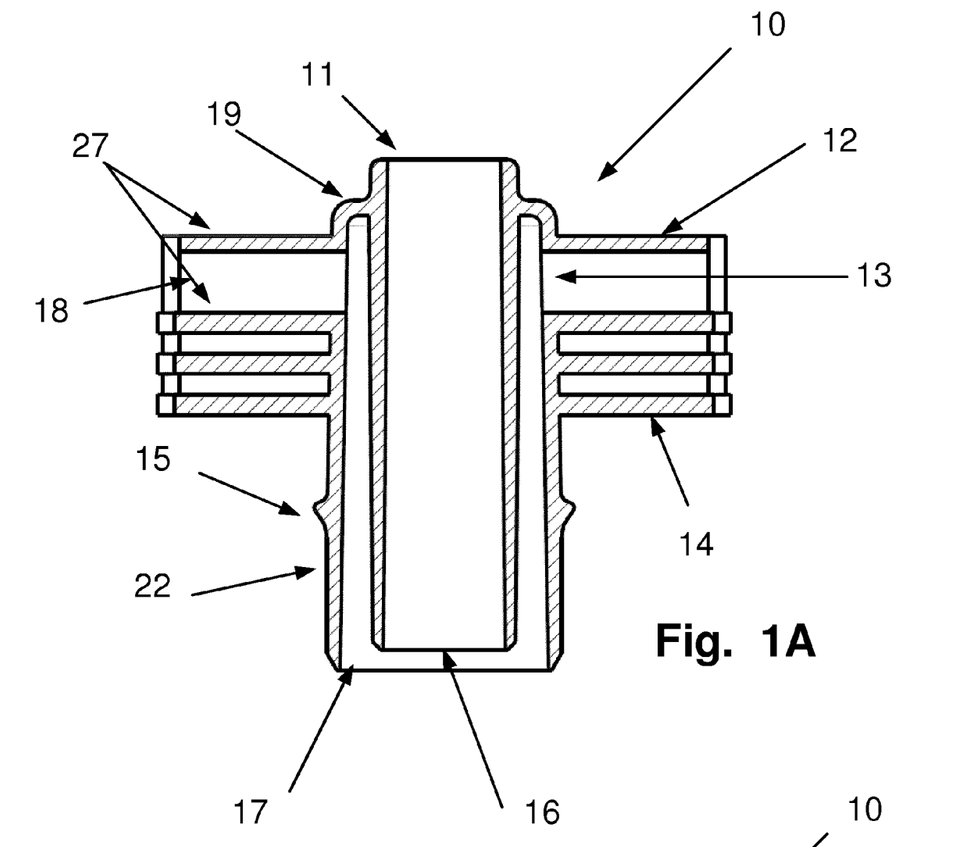
FIG. 1A-D is showing schematic cross-sections of an exemplary embodiment of a connector.
Figure 1B:
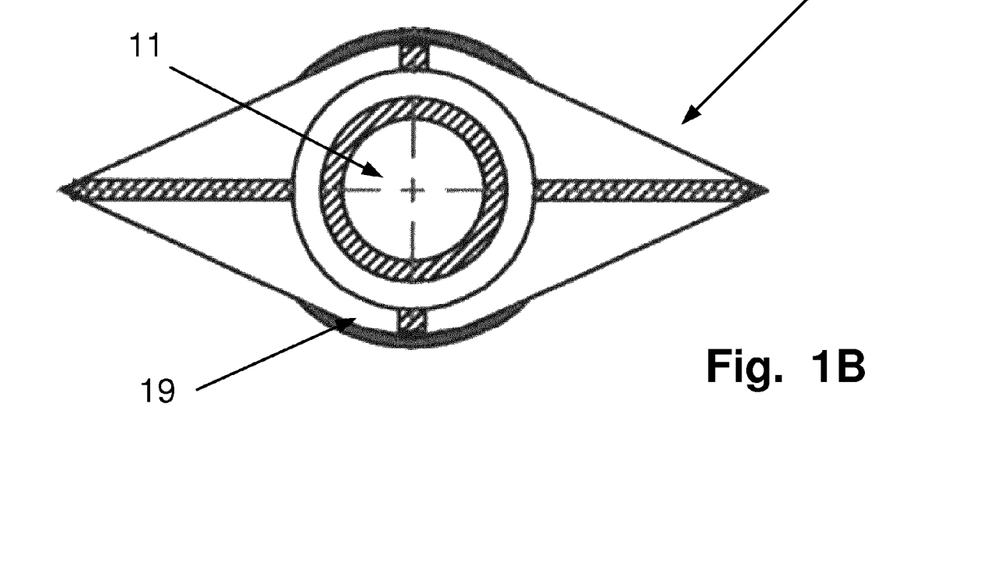
Figure 1C:
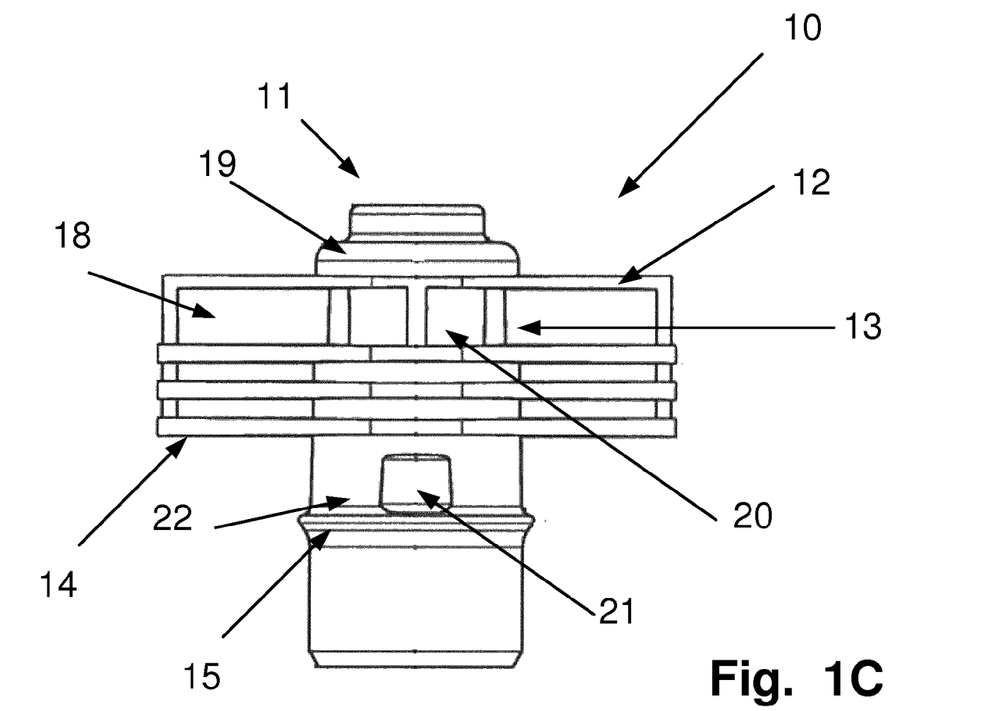
Figure 1D:
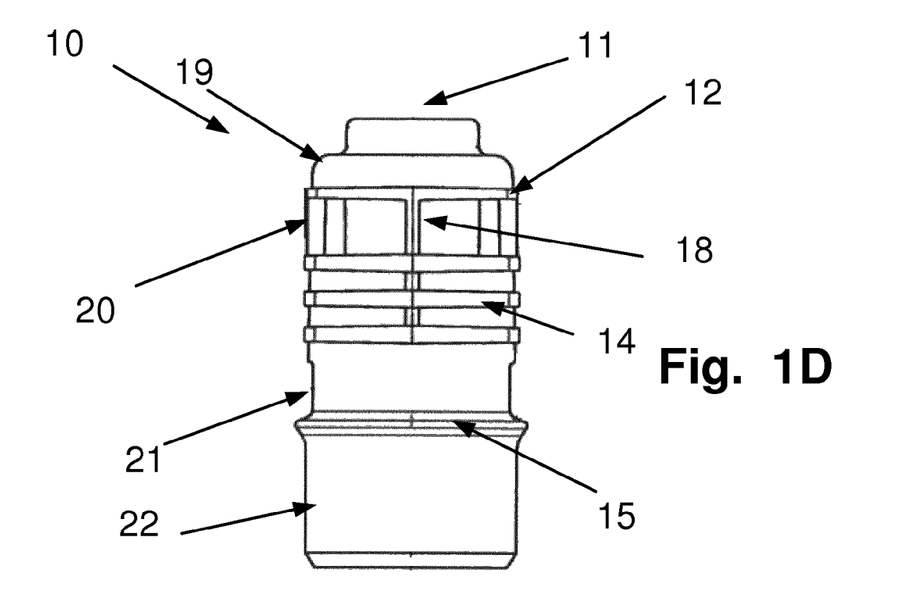
Figure 1E:
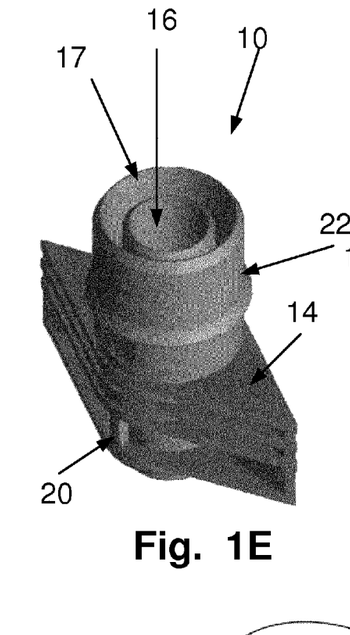
FIG. 1E-F is showing schematic 3D views of an exemplary embodiment of a connector.
Figure 1F:
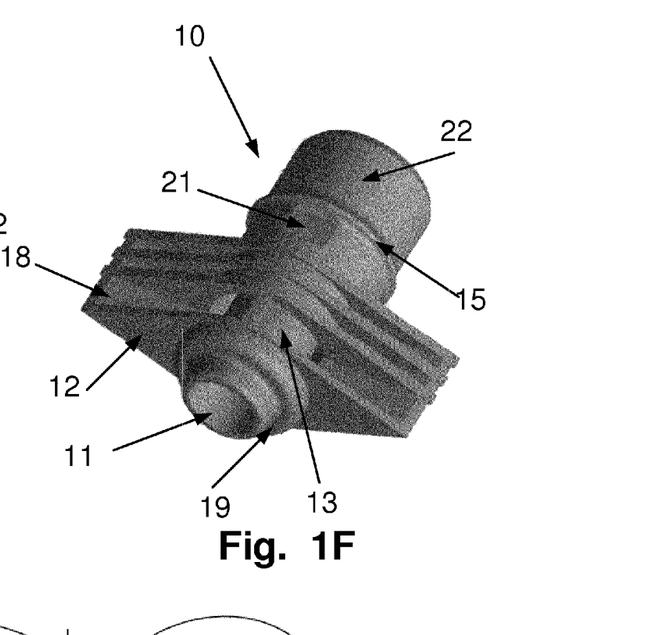
Figure 1G:
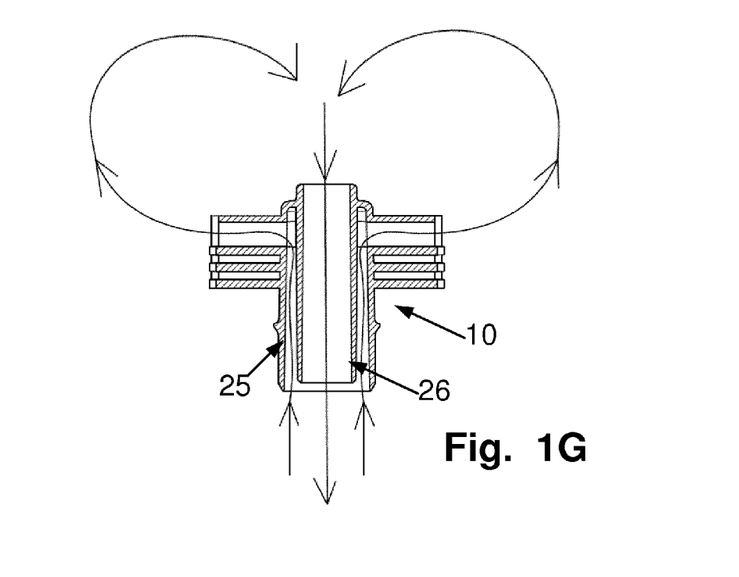
FIG. 1G is showing a schematic cross-section view of an exemplary embodiment of the connector when used as a combined inlet and outlet.

Further, the connector may comprise a protruding member 12 positioned between the distal end of the outer elongated body 22 and the opening 13 being positioned radially outwards from the outer elongated body 22. Additionally and/or alternatively, the protruding member may extend from below radially outward opening 13 to above the opening 13.

The protruding member 12 may have a fastening section 14 which may be positioned in the seam at the bottom of a container. The connector 10 may be fastened by welding through applying heat or by using glue or other suitable joining techniques to the container. Alternatively and/or additionally the fastening section 14 may have a shape being tapered from the outer elongated body 22. Thus a smoother transit between the connector and the seam may be created. Alternatively and/or additionally, the tapered shape of the fastening section 14 may improve the sealing effect, the tightness, of the container material around the connector 10.

Preferably the tapered part may have a wedge shaped or boat-shaped profile with straight walls. Alternatively, it may also be shaped slightly curved, e.g. elliptic, hull-shaped, or wing-shaped.

The upper part of the protruding member 12, positioned above the radially outward opening 13, and the top of the fastening section 14 may be a directing section 27 for directing a fluid in and out of the radially positioned opening 13. The directing section 27 may, in some examples, have an H-shaped profile obtained between the outside of the top part of the fastening section 14 and the top part of protruding member 12. The middle member 18 may improve the directing of the fluid. Alternatively and/or additionally the middle member 18 is positioned to increase the stability of the directing section 27.

The H-shaped profile (see e.g. FIG. 1D) may provide a flow path, being the directing section 27, between the top of the protruding member 12 and the fastening section 14. This arrangement will improve the directing of the flow of a fluid from the radially positioned opening 13 when flowing into the container. Alternatively and/or additionally, the directing section may prevent the material of the container to obstruct the flow in and out of the radially positioned openings 13 of connector 10. The obstruction could for instance occur when a compartment of the container surrounding the connector 10 is empty. This could occur at the initial stage when introducing a fluid into a container. Additionally and/or alternatively, the obstruction could occur when emptying the container and the container may get sucked into the opening 13 of the connector 10. These kinds of obstructions are effectively prevented.

Further, the directing section may include distance units 20, such as two struts, for improving the stability. Alternatively and/or additionally the struts 20 are positioned as spacers to avoid the container to obstruct the radially positioned opening 13.

Additionally, in some examples, a build-up portion 19 may be positioned on-top of the protruding member 12, sealing the outer body against the inner body. The build-up portion 19 is an inner protrusion in the body. When a flow of a fluid hits the inside of the build-up portion 19 the flow may have to go back to exit through the radially positioned opening. Thus a turbulent flow may be created which may increase the pressure of the flow out of the radially positioned opening 13. This provides for advantageously improved mixing.

The distance between the top of the protruding member 12 and the axially positioned opening 11 in the container is decided by the dimensions of the container. Alternatively the distance may be adjusted to suit the dimension of a compartment of the container surrounding the connector 10.

Additional and/or alternative feature in some embodiments of the connector 10 has a ridge 15 located around the outer surface of the elongated body 22 and located outside of the container. The ridge 15 may be used to increase the sealing effect between the connector 10 and a mixing system, for example by use of a mating O-ring.

As an additional and/or alternative feature in some examples of a connector 10, a flat surface 21 may be located on the outside surface of the outer elongated body 22 and outside of the container. The flat surface 21 may be used to efficiently hold the connector 10 in position when attached to a mixing system, for example by engaging with a matingly provided fork-like tool. The connector may thus become efficiently locked to the mixing system. Rotational movement of the connector is prevented as well as longitudinal movement. This may be important when applying high pressure of fluids into the container through the connector 10.

The connector 10 may be operated in at least three operational modes.

In one operational mode, both the opening 16, 17 of the elongated hollow bodies of the connector 10 are used as inlets to the container, to fast provide a volume of a fluid or a high pressure of a fluid into a container.

Additionally and/or alternatively, the flow from the radially positioned opening 13 and the flow from the axially positioned opening 11 will create a tubular motion inside the bag after the dividers have been opened. Hence the dissolvent and mixing will be improved inside the container. Further, this may increase the likelihood of complete rupture of the container's inner seams.

Additionally and/or alternatively the axially positioned opening 11 located inside the container may be closed at one point in time after the initial rupture of the compartment dividers. Hence the turbulent movement may change since it will only be maintained from to the radially flow out of the opening 13 of the connector 10. This turbulent motion in the container may in some cases have an improvement on the mixing, for example it may decrease the likelihood of powder residuals along the inner sides of the container.

In another operation mode (see FIG. 1G), the inner flow channel 26 of the connector is used as an outlet and the outer flow-channel 25 as an inlet. Thus, by using an external pump, a re-circulation may be obtained in and out of the container which may improve the mixing of the content of the container since the re-circulation may be run continuously until sufficient mixing is obtained. During this operation further fluid may be added to the solution if needed but it is not necessary. If further fluid may be added or not depends on the configuration of the mixing system the container is connected to. Alternatively this operation mode may be run in the opposite direction using the inner flow channel 26 as an inlet and the outer flow-channel 25 as an outlet.

In a further operation mode, both flow-channels 25, 26 may be used as outlets to quickly empty the container. Using all openings 11, 13 inside the container as outlets may improve the efficiency of the emptying procedure. The time for emptying the container may thus be decreased. Additionally the amount of solution left in the container when emptied and the container is discharged may be minimized. The speed is improved by using both flow channels as outlets and the amount of solution left in the container is minimized by the opening 13 being radially positioned and preferably located at the lowest point at bottom of the container. Hence, an increased draining of solution from the container may be provided in a cost and time efficient manner.

Alternatively and/or additionally, in some examples of the connector 10, the flow cross-sectional area of the outer flow-channel will slightly decrease from opening 17 to opening 13, such as V-shaped. This can be seen in FIG. 1A. By decreasing the flow cross-sectional area of the flow channel the pressure may increase of the flow out of the radially positioned opening 13.

FIG. 2A-F is showing an exemplary embodiment of a connector 110. The connector 110 is made of an elongated body 122 having interconnected walls to provide two flow channels, preferably being two elongated hollow bodies.

One of the hollow bodies is positioned axially arranged inside the other hollow body.

The bodies may have any shape of its cross-section, such as ellipsoid, or annular, or polygonal etc.

A proximal end of the connector is arranged to be positioned inside a container and a distal end to be positioned outside of the container. At the distal end, the connector is provided with two openings 116, 117. Preferably the openings are annular-shaped, but may additionally and/or alternatively be ellipsoid or polygonal. Additionally one of the bodies may be substantially centrally positioned 116 in relation to the other 117. Additionally, there are at least two openings 111, 113 at the proximal end of the connector 110. One of the openings 111 is positioned along an axis of the connector 110 and the other opening 113 may be a radial tube positioned radially outwards from the outer elongated body 22 and in fluid communication with one of the flow channels. The edge of the inner opening may be longitudinally recessed in relation to the edge of the outer opening. Preferably the radially positioned opening 113 may be two radial tubes directed in opposite directions from the outer elongated body 122.

Further the connector may comprise a protruding member being a fastening section 114, positioned between the distal end of the outer elongated body 122 and the radial tube 113. The fastening section 114 may be positioned radially outwards from the outer elongated body 122.

The fastening section 114 may be positioned in the seam at the bottom of a container for fastening the connector 110 to a container. The connector 110 may be fastened by welding through applying heat or by using glue or other suitable joining techniques. Alternatively and/or additionally the fastening section 114 may have a shape being tapered from the outer elongated body 122. Thus a smoother transit between the connector and the seam may be created. Alternatively and/or additionally, the tapered shape of the fastening section 114 may improve the sealing effect, the tightness, of the container material around the connector 110.

Preferably the tapered part may have a wedge shaped or boat-shaped profile with straight walls. Alternatively, it may also be shaped slightly curved, e.g. elliptic, hull-shaped, or wing-shaped.

The radial tube of the opening 113 is arranged to improve the directing of the flow of a fluid from one of the fluid channels. Alternatively and/or additionally, the radial tube of the opening 113 may prevent the material of the container to obstruct the flow in and out of the radially positioned openings 113 of connector 110. The obstruction could occur when a compartment of the container surrounding the connector 110 is empty. This could occur at the initial stage when introducing a fluid into a container. Additionally and/or alternatively, the obstruction could occur when emptying the container and the container may get sucked into the opening 113 of the connector 110.

Additionally, in some examples, a build-up portion 119 may be positioned on-top of the outer elongated body 122, sealing the outer body against the inner body. The build-up portion 119 is an inner protrusion in the body. When a flow of a fluid hits the inside of the build-up portion 119 the flow may have to go back to exit through the radially positioned opening. Thus a turbulent flow may be created which may increase the pressure of the flow out of the radially positioned opening 113.

The distance between the radial tube of opening 113 and the axially positioned opening 111 inside the container is decided by the dimensions of the container. Alternatively the distance may be adjusted to suit the dimension of a compartment of the container surrounding the connector 110.

Additional and/or alternative feature in some embodiments of the connector 110 has a ridge 115 located around the outer surface of the elongated body 122 and located outside of the container. The ridge 115 may be used to increase the sealing effect between the connector 110 and a mixing system, for example by use of an O-ring.

Additional and/or alternative feature in some examples of a connector, a flat surface 121 may be located on the outside surface of the outer elongated body 122 and outside of the container. The flat surface 121 may be used to hold the connector 110 in position when attached to a mixing system, for example by engaging with a matingly provided fork-like tool. The connector may thus become efficiently locked to the mixing system. Rotational movement of the connector is prevented as well as longitudinal movement. This may be important when applying high pressure of fluids into the container through the connector 110.

Figures 2A, 2B:
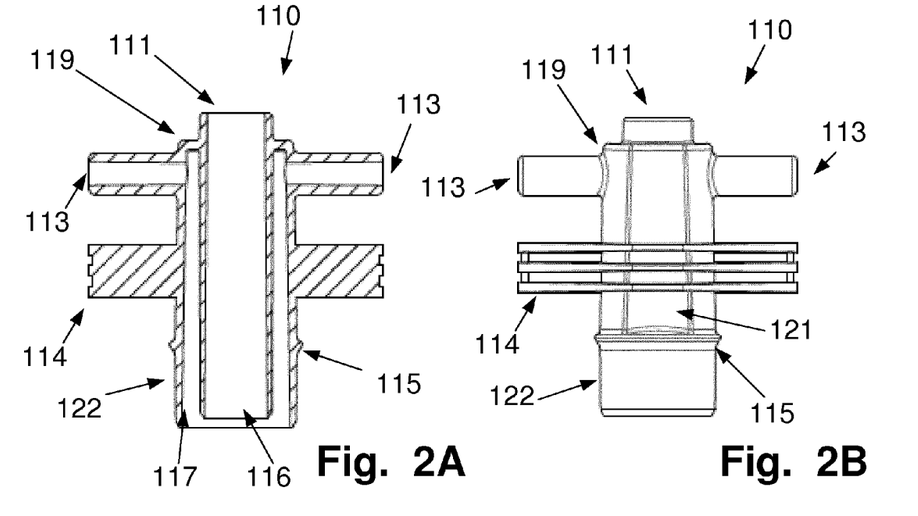
FIG. 2A-C is showing schematic cross-sections of an exemplary embodiment of a connector.
Figure 2C:
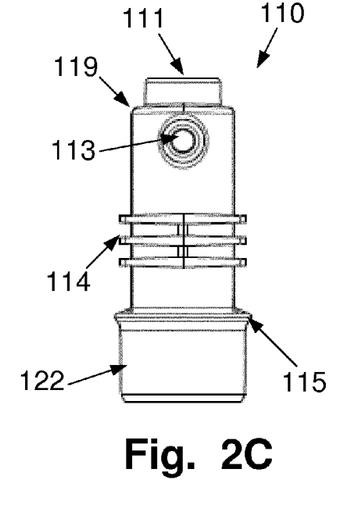
Figure 2D:
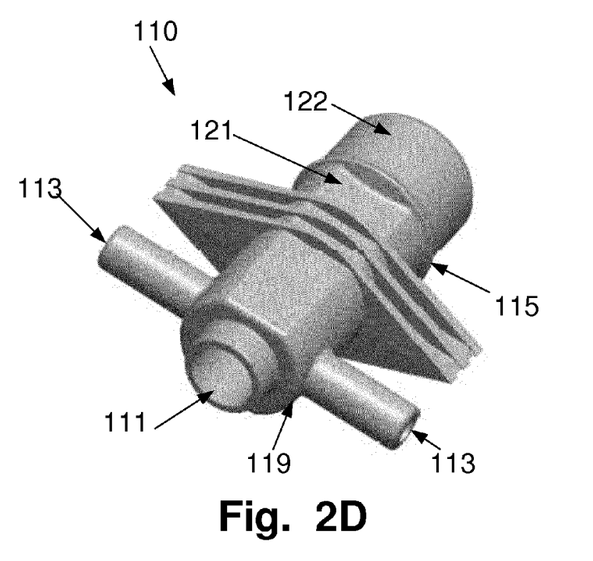
FIG. 2D-E is showing schematic 3D views of an exemplary embodiment of a connector.
Figure 2E:
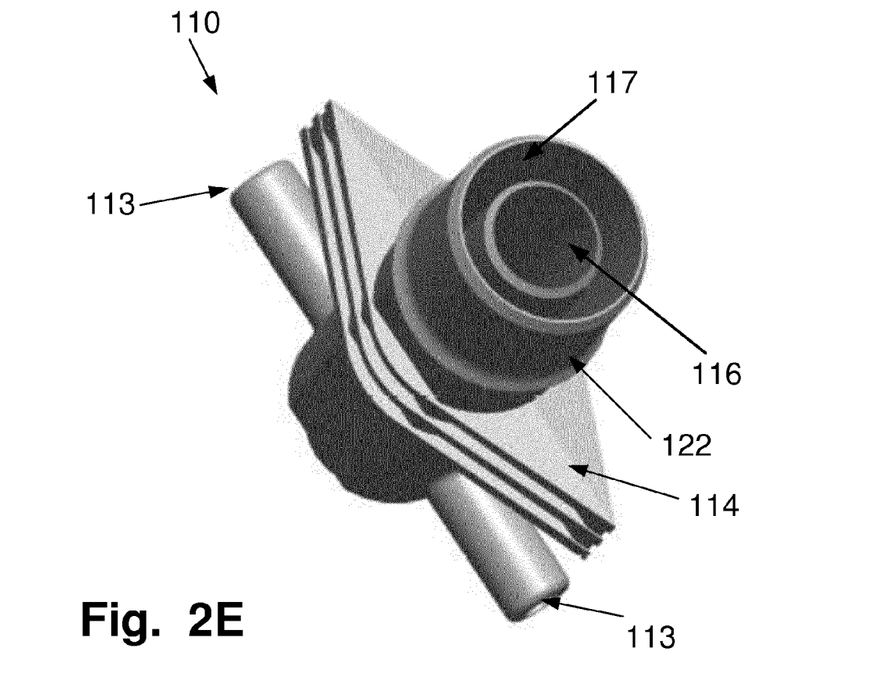
Figure 2F:
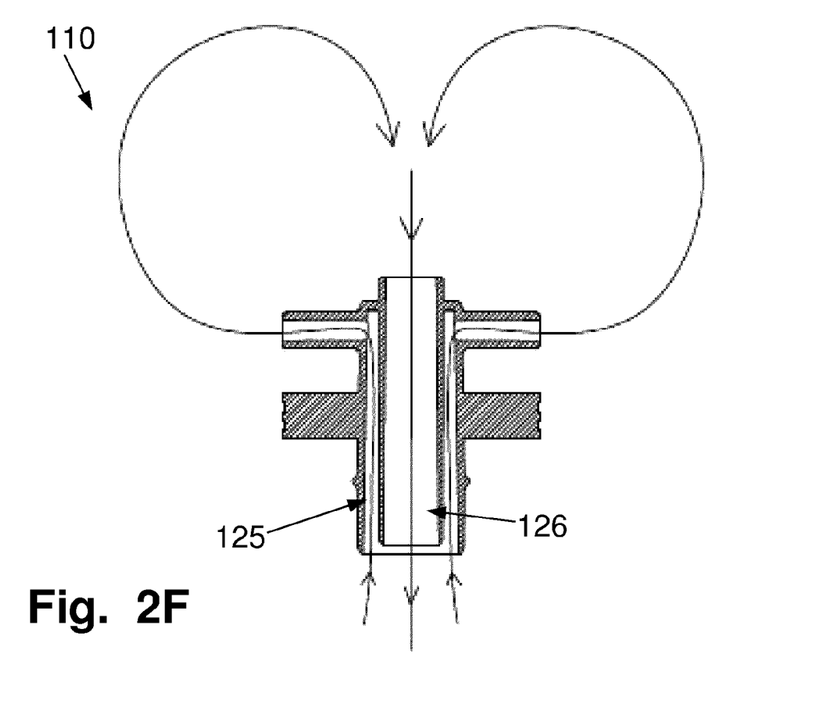
FIG. 2F is showing a schematic cross-section view of an exemplary embodiment of the connector when used as a combined inlet and outlet.

Similar to the connector of FIG. 1A-G, this connector 110 may be operated in at least three operational modes. As an example, FIG. 2F shows the flow through the connector during re-circulation mode were the inner flow channel 126 of the connector is used as an outlet and the outer flow-channel 125 is used as an inlet.

Figure 3A:
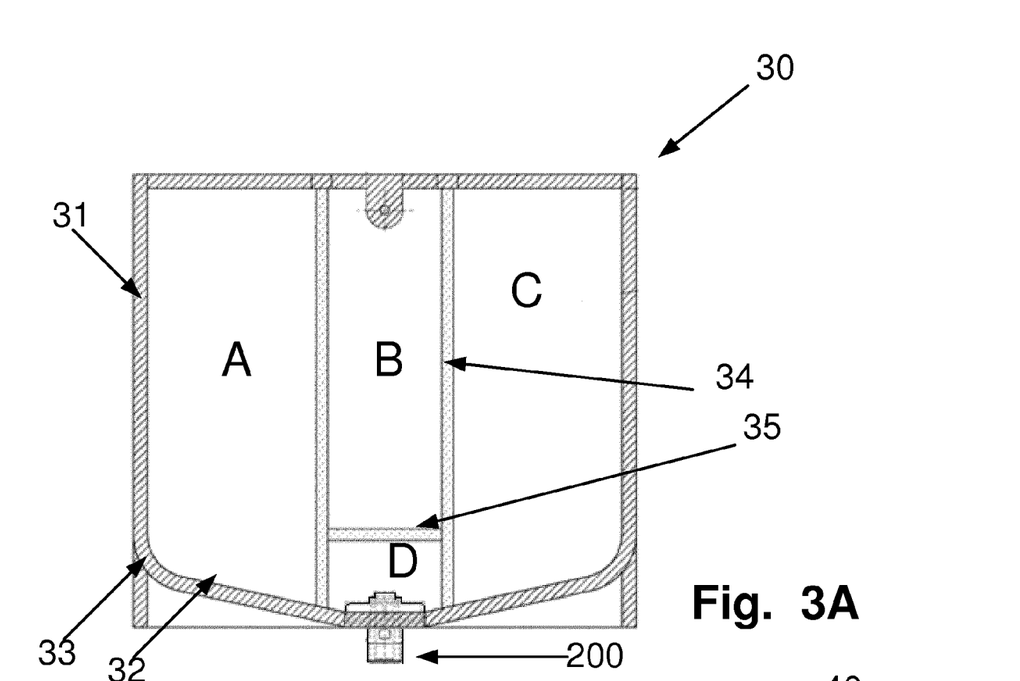
FIG. 3A is showing a schematic illustration of an exemplary embodiment of a container with a connector.
Figure 3B:
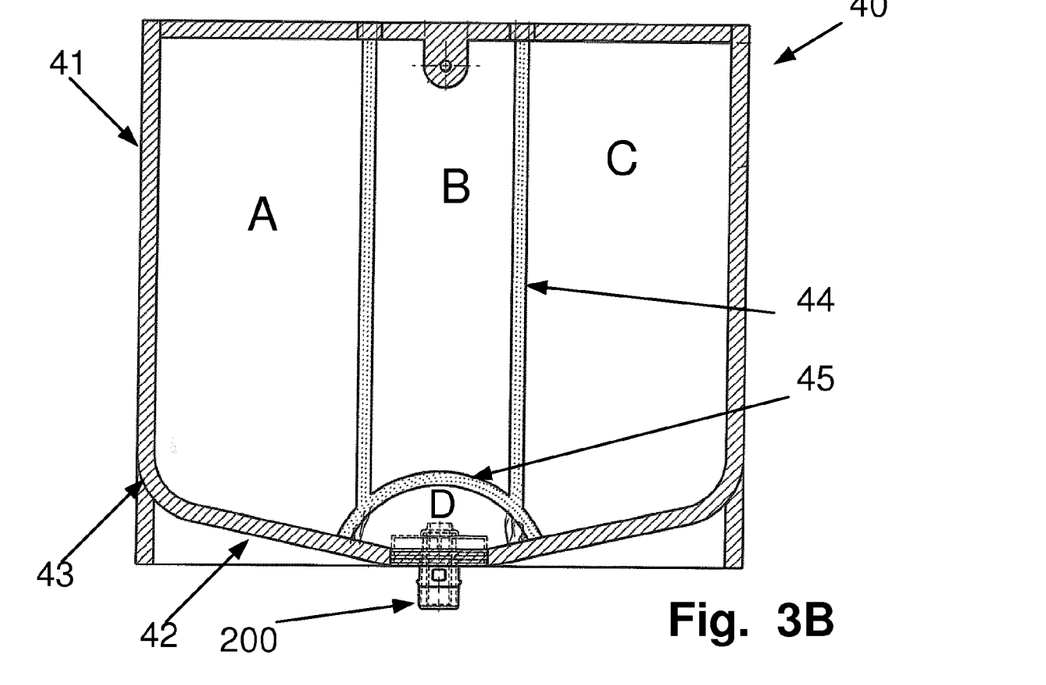
FIG. 3B is showing a schematic illustration of another exemplary embodiment of a container with a connector.
Figure 3C:
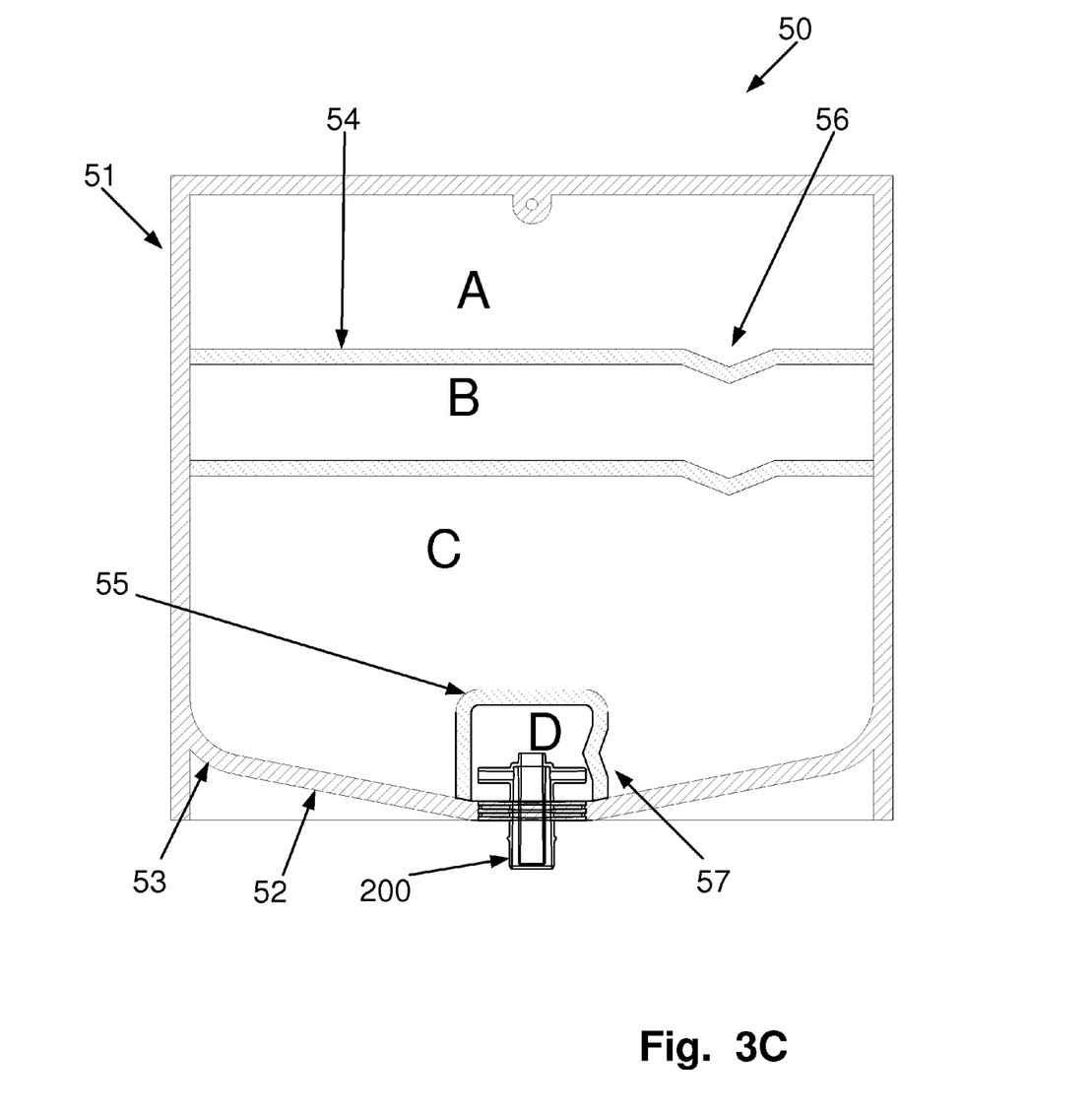
FIG. 3C is showing a schematic illustration of a further exemplary embodiment of a container with a connector.

FIG. 3A-C shows three examples of containers 30, 40, 50 such as a bag, with the connector 200. In FIG. 3A-B the longitudinally positioned compartment dividers 34, 44 are separating the three compartments A, B, C. The compartment dividers may have any shape such as substantially straight, v-shaped or zigzag.

Longitudinally positioned compartment dividers 34, 44 may improve the opening or rupture of the compartment dividers 34, 44 since the opening may be smoother. Additionally the compartment dividers will be closer to the initial opening which will reduce the risk of the compartment dividers 34, 44 not opening at fully adjacent to the walls 31, 41. If not fully opened, there may be an increased risk of powder deposition (i.e. residuals) or aggregations at the locations of where the compartment divides 34, 44 meets the walls 31, 41. This may improve the mixing and the precision of the concentration. Further the concentration may be more even throughout of the container 30, 40 due to the further improved circulation since the interior of the walls 31, 41 may be more even.

Additionally and/or alternatively, the mixing will be improved since longitudinally positioned compartment dividers 34, 44 avoids unopened parts of the compartment dividers adjacent to the interior side of the longitudinal part of the outer walls 31, 41.

Additionally, the container 30, 40 may further comprise an empty compartment D surrounding the connector 200. This could be obtained by a substantially vertically positioned compartment divider 35 ending adjacent to the longitudinally positioned compartment dividers 34, as in FIG. 3A.

Additionally and/or alternatively, in some embodiments the empty compartment D surrounding the connector 200 could be made by a curved compartment divider 45 which either adjacent the longitudinally positioned compartment dividers 45 or adjacent the bottom surface, as in FIG. 3B.

This empty compartment may improve the opening of the longitudinally positioned compartment dividers by providing an initiate even pressure on bottom part of the longitudinally positioned compartment dividers 34, 44 when filled with a fluid by the connector 200.

In FIG. 3C a container 50 is showed having vertically positioned compartment dividers 54. The compartment dividers may have a V-shaped portion 56. The V-shaped portion 56 may improve the opening and/or rupture of the compartment dividers 54. The V-shaped portion 56 may be used to control the opening of the compartment dividers 54. The opening and/or rupture will begin at the tip of the V-shaped portion 56, thus the opening and/or rupture may be smooth and controlled and not explode. Additionally the opening and/or rupture of the compartment dividers will be quiet. If no V-shape portion 56 the compartment dividers 54 may open with a bang.

The V-shaped portion 56 may be positioned anywhere along the compartment dividers 54. By positioning the V-shaped portion closer to the wall were the container is being filled, weakening of the seam and/or unintentional opening and/or rupture may be prevented.

Additionally, similar to the containers in FIG. 3A-B the container in FIG. 3C may comprise a further compartment D being empty. The compartment D may surround the connector 200 by compartment divider 55. Also one of the sides of the compartment D and the compartment divider 55 may have a V-Shaped part 57 to better control the opening and/or rupture.

In FIG. 3A-C, at least one of the compartments contains a powder and the other compartments may contain either powders or liquids. The powders and liquids are provided in suitable amounts for providing a defined solution when mixed with a predetermined amount of fluid from an external supply source. The solution is provided by dissolving the powder in a fluid, such as water, and by mixing the water with the content of the compartments. The fluid is applied through the connector from an external supply source.

The compartment dividers 34, 44, 54 differ from the seam or weld 31, 41, 51 by opening and/or rupture when a pressure of a fluid is applied through the connector 200. The opening and/or rupture of the compartment dividers may be due to directly applied pressure from the flowing fluid. Alternatively and/or additionally the opening or rupture of the compartment dividers may be due to an expansion of a compartment due to an increase in volume of the compartment when a fluid is applied through the connector 200.

The compartment dividers 34, 44, 54 may be controllable opened and/or ruptured by controlling the flow of the fluid through the connector 200.

Additionally and/or alternatively, in some examples the dividers 34, 44, 54 are sequentially opened and/or ruptured. Alternatively all compartments dividers 34, 44, 54 may opened simultaneously.

Additionally and/or alternatively, by varying the strength of the compartment divides 34, 44, 54 for example by increasing the applied heat when welding, the compartment dividers 34, 44, 54 may be opened subsequently.

Additionally, the sizes of the compartments may decide by the amount of powder or liquid content of each compartment needed to obtain the final solution.

The bottom surface 32, 42, 52 of the container 30, 40, 50 may be inclined and has beveled and/or rounded lower edges 33, 43, 53. This may direct the content of the container 30, 40, 50 towards the lower point of the container while the rounded edges 33, 43, 53 may reduce the risk that contents of the container 30, 40, 50 may remain at the walls 31, 41, 51 and in the interior edges of the container 30, 40, 50. This may improve the mixing of the solution.

Additionally and/or alternatively, the inclined bottom 33, 43, 53 in combination with the beveled and/or rounded edges 33, 43, 53 may increase the circulation and improve the mixing action in the container 30, 40, 50, which may improve the mixing of the solution.

Additionally and/or alternatively, the combination of the above described construction of a container 30, 40, 50 with a connector 200 having at least one radially positioned opening directed towards the inclined bottom 33, 43, 53 and beveled edges 33, 43, 53 may further improve the circulation of the fluid during opening of the divides 34, 44, 54, Also, the combination may improve recirculation of the solution, thus improving the mixing of the solution.

Additionally and/or alternatively, the inclined bottom surface 31, 41, 51 of the container 30, 40, 50 may positioning the connector 200 with its radially positioned opening closely at the lowest point of the container 30, 40, 50 and adjacent to the junction of the two inclined surfaces of the container. This increases the efficiency of emptying the container since the solution may flow towards the lower positioned openings.

Figure 4A:
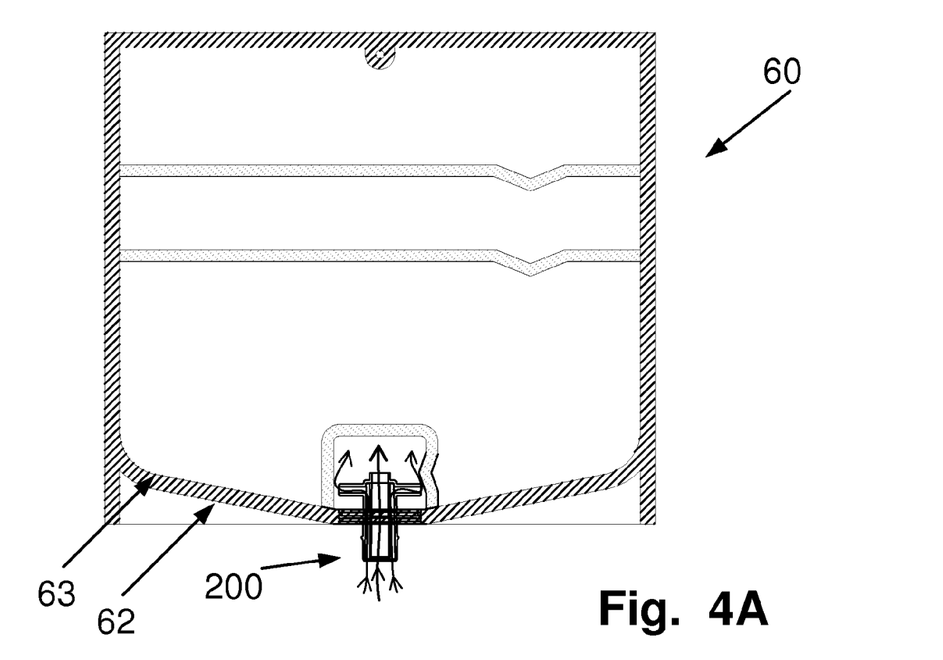
FIG. 4A is showing a schematic cross-section of an exemplary embodiment of a connector fastened to a container when both flow channels are used as inlets.
Figure 4B:
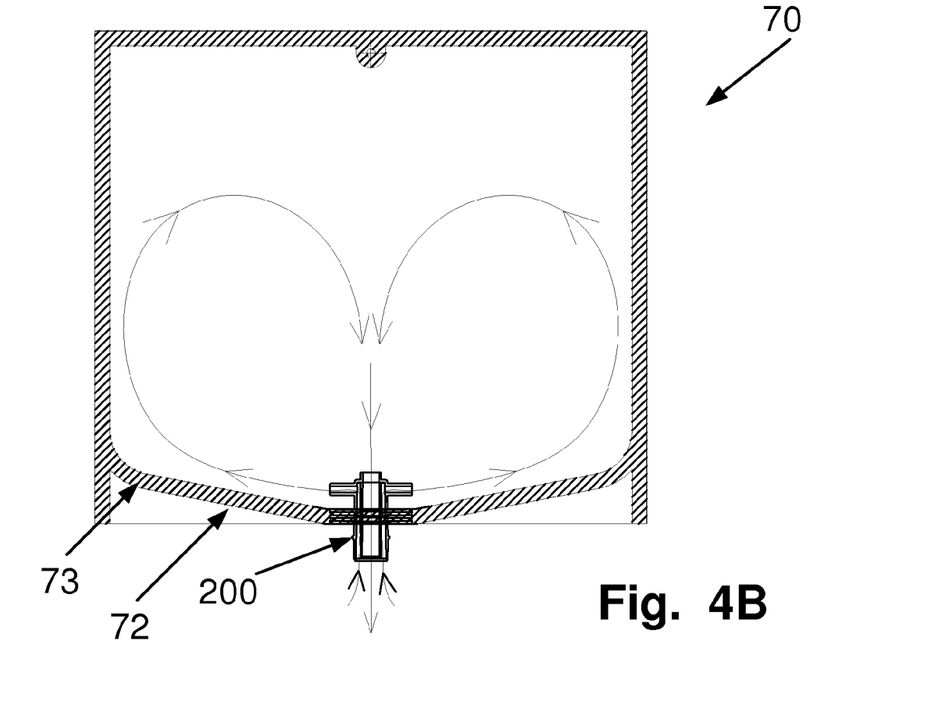
FIG. 4B is showing a schematic cross-section of an exemplary embodiment of a connector fastened to a container and one flow-channel is used as an inlet and another as an outlet, simultaneously.
Figure 4C:
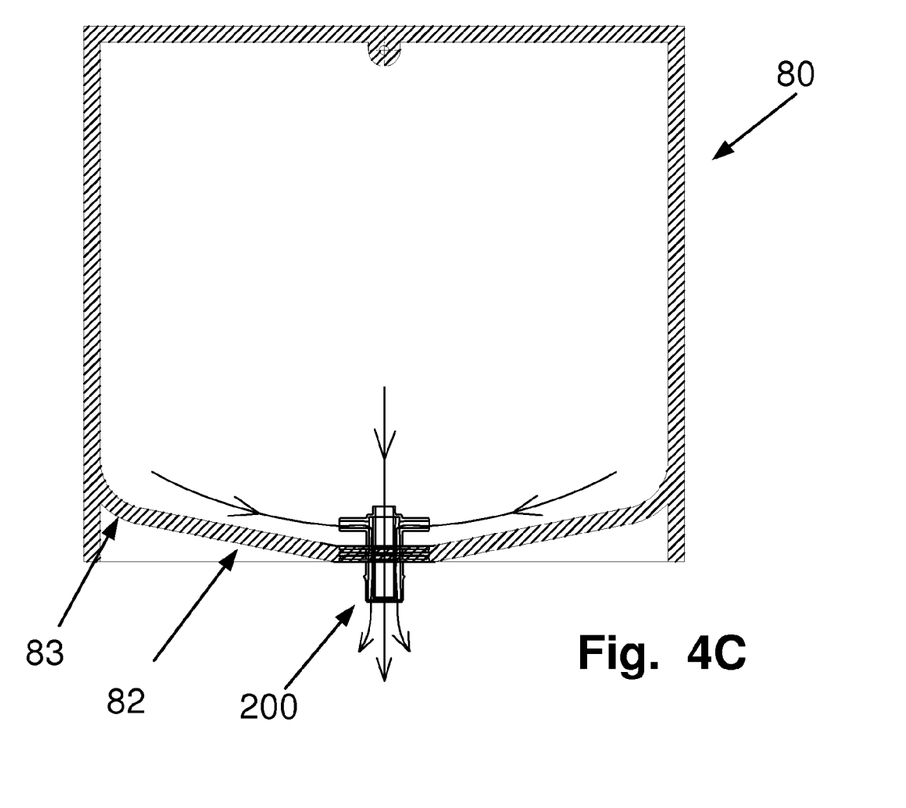
FIG. 4C is showing a schematic cross-section of an exemplary embodiment of a connector fastened to a container when both flow channels are used as outlets and the compartment dividers are ruptured.

FIGS. 4A-C is showing a combination of a container 30, 40, 50 and a connector 200. The figures show examples of different fluid flows and operation modes during different stages of the mixing. The connector 200 may be a connector according to the examples given hereinbefore.

A controlled circling flow pattern improves the mixing in the container. For example, the risk of residuals left along the sides and in the corners of the container may be reduced and the dissolvent of the powders with the applied fluids may increase. Examples of fluid flows are shown in FIGS. 4A-C, showing recirculation and/or circular flow patterns.

In more detail, FIGS. 4A-C are illustrating different mixing modes and stages of the mixing action of the container. The container 60, 70, 80 in combination with a connector 200 may be operated in at least three modes.

In one operation mode, see FIG. 4A, both the opening of the elongated hollow bodies of the connector 200 are used as inlets to the container 60, 70, 80 to fast provide a volume of a fluid or a high pressure into the container 60, 70, 80. This may improve the likelihood of complete opening of the peelable compartment dividers. By applying the fluid radially towards the inclined bottom 62, 72, 82 and beveled edges 63, 73, 83 a pressure will be applied along inside of the longitudinal outer welds thus, the likelihood of a fully peeled compartment divider adjutant the interior walls of the container increases.

Additionally and/or alternatively, the flow from the radially positioned opening and the flow from the axially positioned opening will create a tubular circulation inside the container 60, 70, 80. Hence the dissolvent and mixing will be improved inside the container 60, 70, 80.

Additionally and/or alternatively the axially positioned opening of the connector 200, located inside the container 60, 70, 80, may be closed at one point in time after the initial rupture of the compartment dividers. Hence the circular circulation will change since it will only be maintained from to the radially flow out of radially positioned openings of the connector 200. The radial flow will be directed towards the inclined bottom and beveled edges, thus the circulation pattern will change which may in some cases have an improved effect on the mixing After breaking the empty compartment D mixing with the contents in the first compartment, which comprises a powder, is initiated. A first turbulent circulatory circulation is provided with a high flow rate of fluid through the connector 200 to fill the first compartment with a desired volume. This turbulent circulation may be vicious. Filling the container under high pressure may help to quickly peel the dividers. Further, by filling the compartment fast under turbulent circulation, lumps and/or aggregations of powder particles may be prevented.

In a second operation mode (see FIG. 4B), the axially directed opening of the connector 200 may be used as an outlet and the radially directed flow-channel as an inlet. Thus a re-circulation is obtained in and out of the container 60, 70, 80 which will improve the mixing of the content in the container.

The turbulent circulatory circulation of the recirculation mode is provided as a flow circulation pattern comprising a turbulent flow flowing radially outward from the first channel of the connector, up along an outer edge towards a top section of the container, turning inwardly towards a central section of the container and flowing back down to the connector for leaving the container towards a re-circulation pump via the second channel of the connector, and from the re-circulation pump back to the first channel of the connector for continued internal circulation in the container.

As the bottom surface 62, 72, 82 of the container 60, 70, 80 is inclined and has beveled and/or rounded lower edges 63, 73, 83, the mixing flow in the container is very efficient. This improved mixing action is further improved by combining the described container with the connector 200 which will improve the circulation in the container. Further the archived circulation in the container may reduce the risk that contents, such as powder residuals and/or lumps, remain at the interior walls or interior edges.

Additionally and/or alternatively, this mode may be run before peeling the next divider.

Additionally and/or alternatively, this mode may be run in the opposite direction, using the axially directed opening of the connector 200 as an inlet and the radially directed flow-channel as an outlet.

In a third operation mode, see FIG. 4C, both flow-channels will be used as outlets to empty the container 60, 70, 80. A high out flow may thus be provided without the need of additional outlets. The use of two openings of the connector 200 inside the container as outlets may improve the efficiency of the emptying procedure. The time for emptying the container could be decreased. Further the amount of residual solution left in the container when emptied and the container is discharged may be minimized.

The speed of the emptying process is improved by using both flow channels as outlets and/or the amount of solution left in the container 60, 70, 80 is minimized by the openings being radially positioned. The preferred located are adjutant to bottom of the container.

The inclined bottom 62, 72, 82 of the container 60, 70, 80 positioning the connector 200 with its radially positioned opening close to the lowest point of the container and adjacent to the junction of the two inclined surfaces. This increases the efficiency of emptying the container since the solution may flow towards the lower positioned openings. Thus, the inclined bottom 62, 72, 82 directing the flow towards the radial openings of the connector 200.

Hence, the mixing efficiency is significantly improved when using a connector according to the examples described here. The mixing efficiency is further improved by having and inclined bottom surface of the container to which the connector is connected. The compartment dividers are smoothly opened by a pressure created and causing peeling of the dividers. As the dividers open completely, they risk of leaving non dissolved residues is minimal. Thanks to the design of the container, there are no or little possibilities for residuals to be stuck to corners or to the compartment dividers. Thus the accuracy of the concentrations in the final solution may also be improved by the connector and container described herein.

Additionally, using a container with vertically positioned peelable dividers, any remaining residuals may fall down or be washed down to the connector outlet.

The container may be Z-folded to save space during transport or storage prior to the mixing action. When emptied, it may be folded again to save space for recycling or disposal.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

What is claimed is:

1. A container for mixing an enclosed medical agent with a fluid, comprising:
   an inclined bottom seam directed towards a connector, said connector comprising:
   an elongated hollow body having a plurality of interconnected walls defining a first and a second longitudinal flow channel for fluidly connecting an inside and an outside of said container,
   wherein said first flow channel has a first opening and a second opening, said first opening of said first flow channel is devised to be arranged inside of said container and said second opening of said first flow channel is devised to be arranged outside said container,
   wherein said first opening of said first flow channel is arranged radially outwards from said first flow channel and directed towards said inclined bottom seam;
   said second flow channel has a first opening devised to be arranged inside of said container and a second opening devised to be arranged outside said container arranged axially to said first opening of said second flow channel; and wherein said first opening of said first flow channel and said first opening of said second flow channel are fluidly connected to a compartment of said container.

2. The container according to claim 1, wherein an outer surface of a wall of said first flow channel comprises a tapered protruding member comprising a fastening section for fastening said connector device to said bottom seam of said container.

3. The container according to claim 2, wherein said tapered protruding member further comprising a directing section positioned adjacent to said first opening of said first flow channel for directing a flow of a fluid through said first opening of said first flow channel.

4. The container according to claim 1, wherein said first opening of said first flow channel has a radial tube.

5. The container according to claim 1, wherein said connector comprises two first openings of said first flow channel having radial tubes directed in opposite directions.

6. The container according to claim 1, wherein said first opening of said first flow channel is circumferentially positioned around an outer surface of a wall of said first flow channel.

7. The container according to claim 1, wherein said first flow channel has an axially decreasing flow cross-section towards said first opening.

8. The container according to claim 1, wherein a first wall surrounding said second flow channel is conically tapering towards said outside of said container and said first wall is an interior wall of said first flow channel and a second wall is surrounding said first flow channel without tapering to provide said axially decreasing flow cross-section.

9. The container according to claim 2, wherein said fastening section is adapted to be attachable to said inclining bottom seam of said container.

10. The container according to claim 3, wherein said directing section is further including a distancing unit for keeping a wall of said container at a distance from said first opening of said first flow channel.

11. The container according to claim 1, wherein said first flow channel is a first elongated body and said second flow channel is a second elongated body, wherein said second elongate body is arranged longitudinally inside said first elongate body and having a first end and a second end.

12. The container according to claim 11, wherein first ends of said first and second elongate bodies are axially offset.

13. The container according to claim 11, wherein said second elongate body is arranged coaxially inside said first elongate body.

14. The container according to claim 11, wherein said second fluid channel is a central through channel.

15. The container claim 11, wherein said fluid connector device is a combined inlet and outlet connector, and/or said first and second elongate bodies are integrally in a single monolithic unit.

16. The container according to claim 1, wherein said first opening of said second flow channel is axially offset towards an interior from said first opening of said first flow channel; or wherein said first opening of said second flow channel is axially offset towards said interior from said first opening of said first flow channel, and wherein an internal axial recess is arranged at said first flow channel's first opening.

17. The container according to claim 3, wherein said directing section is arranged for providing a substantially lateral flow entering said container when said first flow channel is an inlet.

18. The container according to claim 1, wherein said container comprises a compartment divider separating each of at least two compartments.

19. The container according claim 18, whereby said compartment divider is configured to controllably open when a pressure of fluid is applied through said connector.

20. The container according claim 18, wherein at least one compartment comprises a powder.

21. The container according claim 18, wherein said compartment divider is positioned substantially longitudinally.

22. The container according claim 18, wherein said compartment divider is positioned substantially vertically.

23. The container according to claim 18, wherein said compartment divider is peelable compartment dividers arranged to releasably separate at least three compartments of said container.

24. The container according to claim 18, wherein said container is a flexible bag.

25. The container according to claim 18, wherein said compartment divider is arranged to open completely when enough pressure of a fluid is applied.

26. The container according to claim 18, wherein said compartment divider is adapted to open either simultaneously and/or subsequently in a defined sequence.

27. A method for obtaining a medical solution by using said container of claim 1, the method comprising:
a first operation mode comprising
introducing a flow of a fluid into said container through the first and/or second flow channel of said connector communicating with a fluid source;
opening compartment dividers of an empty compartment and subsequently compartment dividers by a pressure created by a volume of fluid introduced into said container through said connector,
obtaining a turbulent circulatory circulation in said container by directing said flow of said fluid towards the inclined bottom seam and/or beveled edges of said container, and
stopping said introduction of said fluid when a predetermined volume is introduced into said container; and
a second operation mode comprising
mixing a content of said container including said introduced fluid by re-circulation of said content for obtaining said medical solution, including simultaneously using said connector as an combined inlet and outlet for said re-circulation by said first channel operating as an inlet radially directing said fluid towards said inclined bottom seam and/or beveled edges, and said second channel as an outlet, whereby a second turbulent circulatory circulation is obtained in said container for said mixing.

28. The method according to claim 27, wherein said second turbulent circulatory circulation is a flow circulation pattern comprising a turbulent flow flowing radially outward from said first flow channel of said connector, up along an outer edge towards a top section of said container, turning inwardly towards a central section of said container and flowing back down to said connector for leaving said container towards a re-circulation pump via said second flow channel of said connector, and from said re-circulation pump back to said first flow channel of said connector for continued internal circulation in said container.

29. A method for emptying a provided medical solution obtained according to claim 27, comprising:
stopping said re-circulating action;
emptying said medical solution from said container through said connector in a third operation mode, wherein said first flow channel and said second flow channel of said connector are outlets.

* * * * *

UNITED STATES PATENT AND TRADEMARK OFFICE
CERTIFICATE OF CORRECTION

PATENT NO. : 9,539,175 B2
APPLICATION NO. : 14/127826
DATED : January 10, 2017
INVENTOR(S) : Per-Olov Carlsson et al.

Page 1 of 1

It is certified that error appears in the above-identified patent and that said Letters Patent is hereby corrected as shown below:

In the Specification

Column 5, Line 51, "which" should be --which:--.

Column 8, Lines 23-24, "matingly" should be --mattingly--.

Column 10, Line 38, "matingly" should be --mattingly--.

Column 13, Line 19, after "mixing" insert --.--.

In the Claims

Column 15, Line 50 (approx.), Claim 15, after "container" insert --according to--.

Column 16, Line 1, Claim 19, after "according" insert --to--.

Column 16, Line 4, Claim 20, after "according" insert --to--.

Column 16, Line 6, Claim 21, after "according" insert --to--.

Column 16, Line 8, Claim 22, after "according" insert --to--.

Signed and Sealed this
Eighteenth Day of April, 2017

Michelle K. Lee
*Director of the United States Patent and Trademark Office*